United States Patent [19]

Söder et al.

[11] 3,983,712

[45] Oct. 5, 1976

[54] METHOD OF PRESERVING TEETH WITH ATTACHED LIVE ROOT MEMBRANE

[76] Inventors: Per-Östen Söder, Gronviksvagen 48, S-161 40 Bromma; Lennart A. T. Wieslander, Yngvevagen 3, S-182 64 Djursholm, both of Sweden

[22] Filed: Mar. 25, 1975

[21] Appl. No.: 561,953

[30] Foreign Application Priority Data

Mar. 27, 1974 Sweden .............................. 7404148

[52] U.S. Cl. .................................. 62/65; 32/10 A; 62/78; 128/92 G; 195/1.7
[51] Int. Cl.² ......................................... F25D 13/04
[58] Field of Search ........... 32/10 A; 128/1 R, 92 G; 195/1.7, 1.8; 62/62, 64, 65, 78

[56] References Cited
UNITED STATES PATENTS 3,303,662   2/1967   Moline et al. ............................ 62/62

OTHER PUBLICATIONS

R. J. Coburn et al., *The Development of an Experimental Tooth Bank using Deep Freeze and Tissue Culture Techniques,* Journal of Oral Therapeutics and Pharmacology, vol. 2, 1966.

*Primary Examiner*—William F. O'Dea
*Assistant Examiner*—Ronald C. Capossela
*Attorney, Agent, or Firm*—Fred Philpitt

[57] ABSTRACT

The invention is concerned with a method of preserving extracted teeth with attached live root membrane. After treating the teeth in order to eliminate bacteria and fungi in a nutrient solution to preserve the viability of the root membrane cells the teeth are subjected to a freezing process in two stages and in the presence of a similar nutrient fluid, the temperature being lowered slowly in the first stage to a value between −20° and −50°C and rapidly in the second stage to a value below −50°C, preferably below −150°C.

6 Claims, No Drawings

METHOD OF PRESERVING TEETH WITH ATTACHED LIVE ROOT MEMBRANE

The present invention refers to a method of preserving teeth with attached live root membrane.

In extracting healthy teeth, e.g. in operations for straightening irregular teeth or in the involuntary removal of teeth, it is often desired to reinsert one or more of these teeth in the patient's mouth after some time during which the teeth have been in storage. To make this possible it is essential that the viability of the cells in the membrane surrounding the root be preserved. A method of preserving the viability of the cells in vitro for a long period is already known. It has here even been possible to make the cells multiply. For this purpose the tooth is treated after extraction both to provide the cells with the necessary sustenance for them to preserve their viability and to prevent infections arising through the activities of bacteria and fungi.

The purpose of the present invention is to make possible the transport of the tooth over a relatively long distance to a depot where it is stored and from where it is then returned to a place for reinsertion in the mouth of the patient.

For this purpose, the invention is characterized in that after treating with a method known per se to eliminate bacteria and fungi in the presence of a nutrient solution to preserve the viability of the root membrane cells during this treatment, the tooth is subjected to freezing in the presence of a similar nutrient fluid in two stages of which the first embraces a relatively slow, gradual reduction of the temperature to a value between $-20$ and $-50°$ C, and the other a relatively rapid cooling to a temperature below the first temperature.

The treatment known per se for eliminating bacteria and fungi under conditions chosen to preserve the viability of the root membrane cells is primarily intended for use in immediate connection with the extraction or removal of the tooth after which the tooth and the treatment fluid can be sent to a depot/laboratory for the preservation and storage of teeth. After removal of the nutrient fluid containing antibiotics and the substitution of a new nutrient fluid containing no antibiotics, the tooth is ready for preservation. It is subjected to a freezing operation in accordance with the scheme outlined above, i.e. freezing in two stages of which the first is gradual at a controlled speed and the other more rapid. In a frozen condition the tooth can be stored without any loss of viability almost indefinitely. It may be considered surprising that the tooth can be subjected to the above freezing operation without cracking of the enamel and that the tissues remain attached to it. After a long period of storage in the depot the tooth can be taken out of cold-storage and be allowed to reach room temperature without any precautionary measures with respect to the temperature. The tooth can then be sent to a dental surgeon for reinsertion in the mouth of the patient. Before this happens, the fluid in which the tooth has been stored must normally be removed since it may contain antigenic substances which aggravate processes connected with the reinsertion of the tooth. For this purpose a suitable buffer mixture with a physiological pH value can be used. A particularly useful step here can be to send a suitable quantity of the buffer solution in question along with the container in which the tooth is transported to the place for the operation. In this way the work of the operating theatre is greatly facilitated.

According to the invention the tooth can be stored after freezing in the second stage at a temperature lower than the lowest temperature in the first stage. Here it can be suitable to freeze the tooth in the second stage to a temperature between $-50°$ and $-250°$ C. In the second stage the tooth is preferably cooled to a temperature between $-150°$ and $-200°$ C. As mentioned, cooling in the first stage takes place gradually at a relatively low rate per minute. A suitable value is somewhere between 0.5 and 3 degrees Celcius, favorable results having been obtained at a cooling rate of approx. 1 degree Celcius per minute. Cooling in the first stage can thereby continue until approx. $-30°$ C has been reached after which the temperature in the second stage is rapidly lowered to approx. $-195°$ C by, for example, immersion in a bath of liquid nitrogen.

EXAMPLE

During an operation for straightening irregular teeth a number of healthy teeth were removed from the patient by extraction. Immediately after extraction, the teeth were placed in tissue culture tubes containing Eagle's medium mixed with 10 % calf serum, 4 mM L glutamine, 1 mM sodium salt of $\alpha$-keto propionic acid and sodium bicarbonate in sufficient quantity to give a pH value of 7.0. In order to eliminate bacteria and fungi the following antibiotics in the following concentrations were added:

Penicillin 100 IE/ml, Streptomycin 100 $\mu$g/ml, kanamycin 10 $\mu$g/ml, aureomycin 10 $\mu$g/ml, mycostatin 10 $\mu$g/ml and fungizon 1.0 $\mu$g/ml.

The tubes were then sent by rail to a laboratory, the journey taking 20 hours. Immediately after arrival at the laboratory the nutrient fluid was exchanged for a nutrient fluid of the same composition as above but without the antibiotics.

The teeth were then placed in tubes containing a relatively small quantity of Eagle's medium containing dimethyl sulphoxide. The tubes containing the teeth were chilled to $+4°$ C in 30 minutes. The tubes were then transferred to an alcohol bath at $4°$ C. Dry ice was stirred into the alcohol at a freezing rate of $1°$ C/min. down to $-30°$ C. The tubes were then placed directly in liquid nitrogen at a temperature of $-196°$ C and stored for a relatively long time.

After storage the teeth were immediately placed in a flask containing Eagle's medium at a temperature of $37°$ C. After transportation to a dental surgeon the teeth could be reinserted in the mouth of the same patient from whom they had previously been removed.

What is claimed is:

1. A method for preserving a tooth having attached live root membrane which comprises the steps of
   1. immersing said tooth in a liquid containing known tooth nutrients and antibiotics which will eliminate bacteria and fungi that might result from the tooth being in a nutrient solution,
   2. transporting the tooth while it is immersed in said nutrient liquid containing antibiotics to a tooth bank,
   3. upon arrival at the tooth bank replacing said nutrient liquid containing antibiotics with a nutrient liquid that does not contain antibiotics,
   4. in a first cooling stage cooling the tooth and surrounding nutrient material at a rate of 0.5°–3° Celcius per minute until a first temperature within the range of between −20° and −50° C is attained.

5. in a second cooling stage rapidly cooling said tooth and surrounding nutrient material below said first temperature to a second temperature that is below −50° C but not below −250° C, 6. storing said tooth at said second temperature in said tooth bank.

2. A method according to claim 1 wherein said second temperature is between −150° C and −200° C.

3. A method in accordance with claim 1, wherein the temperature in the first freezing stage is lowered gradually at a rate of approximately 1° C/minute down to a value of approximately −30° C, after which the temperature in the second stage is rapidly reduced to approximately −195° C.

4. A method in accordance with claim 1 wherein freezing is allowed to occur in the presence of a fluid containing a substance which prevents the formation of crystals.

5. A method in accordance with claim 3 characterized in that the substance preventing the formation of crystals is dimethyl sulphoxide.

6. A method according to claim 1 wherein said nutrient liquid comprises Eagle's medium.

* * * * *